United States Patent [19]

McGuire

[11] Patent Number: 4,585,363
[45] Date of Patent: Apr. 29, 1986

[54] THERAPEUTIC AID

[76] Inventor: Kevin C. McGuire, 321 Speedway, Missoula, Mont. 59802

[21] Appl. No.: 613,215

[22] Filed: May 23, 1984

[51] Int. Cl.⁴ .......................... B43K 29/00; A61F 2/68
[52] U.S. Cl. .......................................... 401/6; 623/65; 272/67; 401/48
[58] Field of Search .......................... 434/166; 3/12.8; 128/25 R; 272/67, 68; 401/6, 48; 33/18 R; 362/382, 384, 395, 401, 410, 413; 403/90; 623/65

[56] References Cited

U.S. PATENT DOCUMENTS

| 46,827 | 3/1865 | Squeir | 434/166 |
|---|---|---|---|
| 251,206 | 12/1881 | Forbush . | |
| 389,053 | 9/1888 | Brown | 434/166 |
| 745,100 | 11/1903 | Forbush . | |
| 791,020 | 5/1905 | Forg | 362/401 X |
| 1,695,009 | 12/1928 | Cochran | 623/65 X |
| 3,239,184 | 3/1966 | Kirkeby | 362/401 X |
| 3,425,140 | 2/1969 | Dillon | 434/162 |
| 3,653,775 | 4/1972 | Ross | 401/6 |
| 3,690,020 | 9/1972 | McBratnie | 434/163 |
| 3,824,022 | 7/1974 | Mancino | 401/6 |
| 3,929,462 | 12/1975 | Karmin | 434/162 |
| 4,111,566 | 9/1978 | Kenwell | 401/48 X |
| 4,222,680 | 9/1980 | Browning | 403/90 X |
| 4,238,818 | 12/1980 | Gindel | 362/413 |
| 4,357,717 | 11/1982 | Puhl | 623/65 |

Primary Examiner—Richard J. Apley
Assistant Examiner—Alan W. Cannon
Attorney, Agent, or Firm—Wells, St. John & Roberts

[57] ABSTRACT

A therapeutic device for use by a patient in developing fine, medium and gross motor arm movements. The device can be clamped to a stationary surface such as chair or desk and includes outwardly extending upper and forearm members. They are pivotably joined for movement through prescribed angles at joints partially simulating the joints of the arm. The joints each include selective resistance adjustments that enable a selective resistance to be applied at each joint according to the needs of the patient. A grip member at an outer or distal end of the forearm member is grasped or otherwise attached to the patient's hand during use. Movements of the hand and arm effect corresponding movements through the joints of the device. The device thus acts to dampen sudden movements and exercise selected muscle groups while moving in direct response to movement of the user's arm.

24 Claims, 11 Drawing Figures

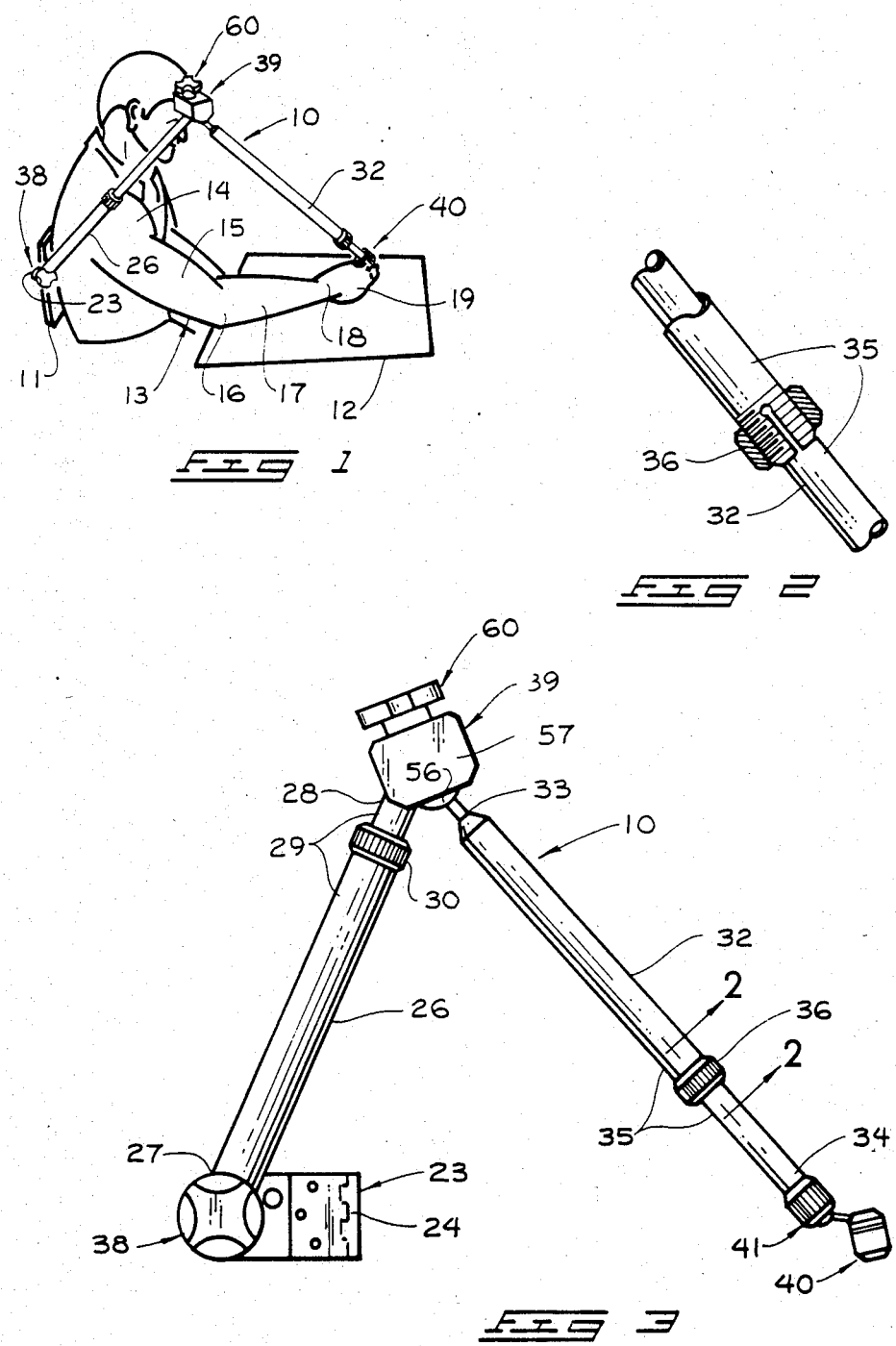

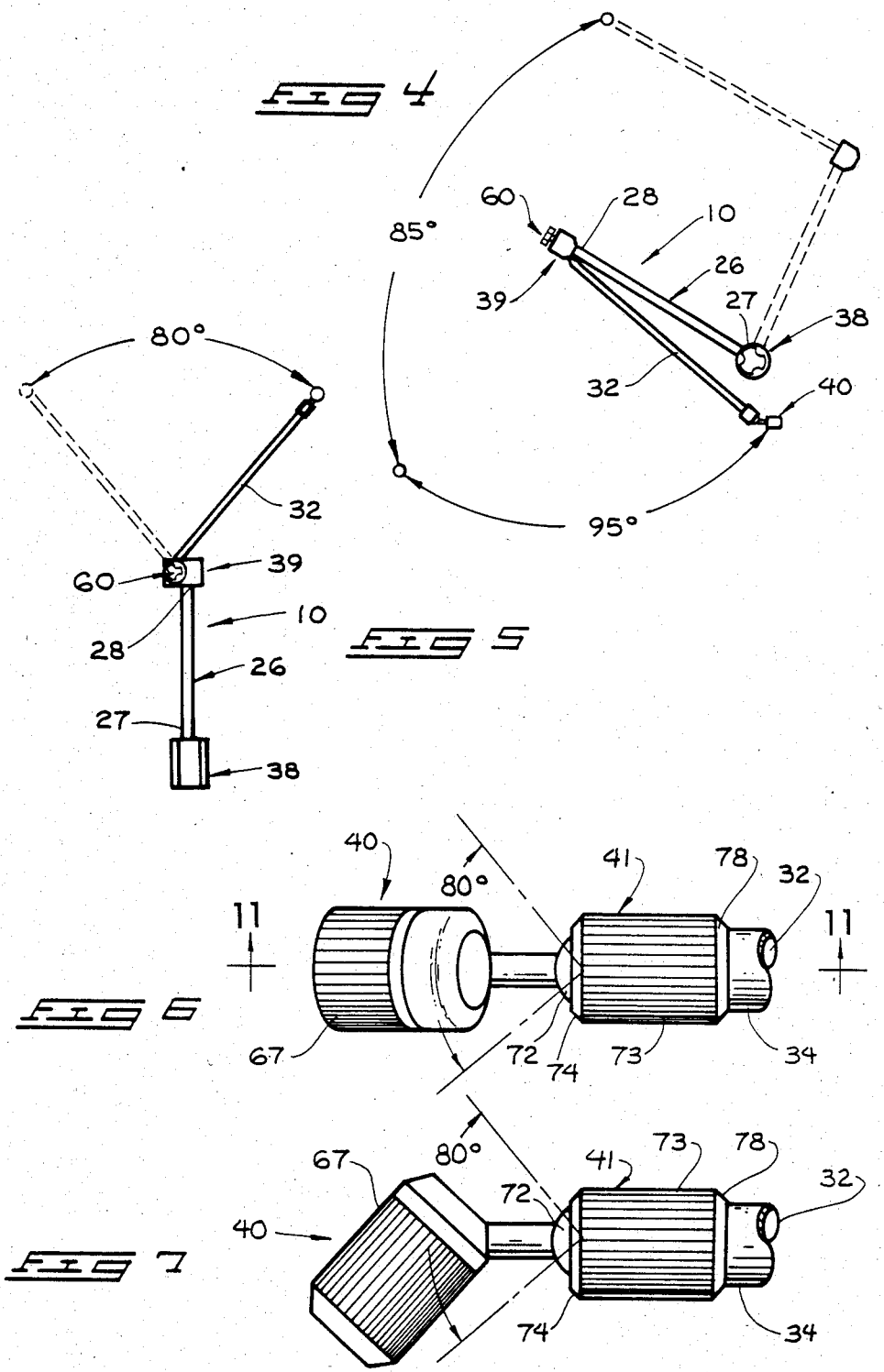

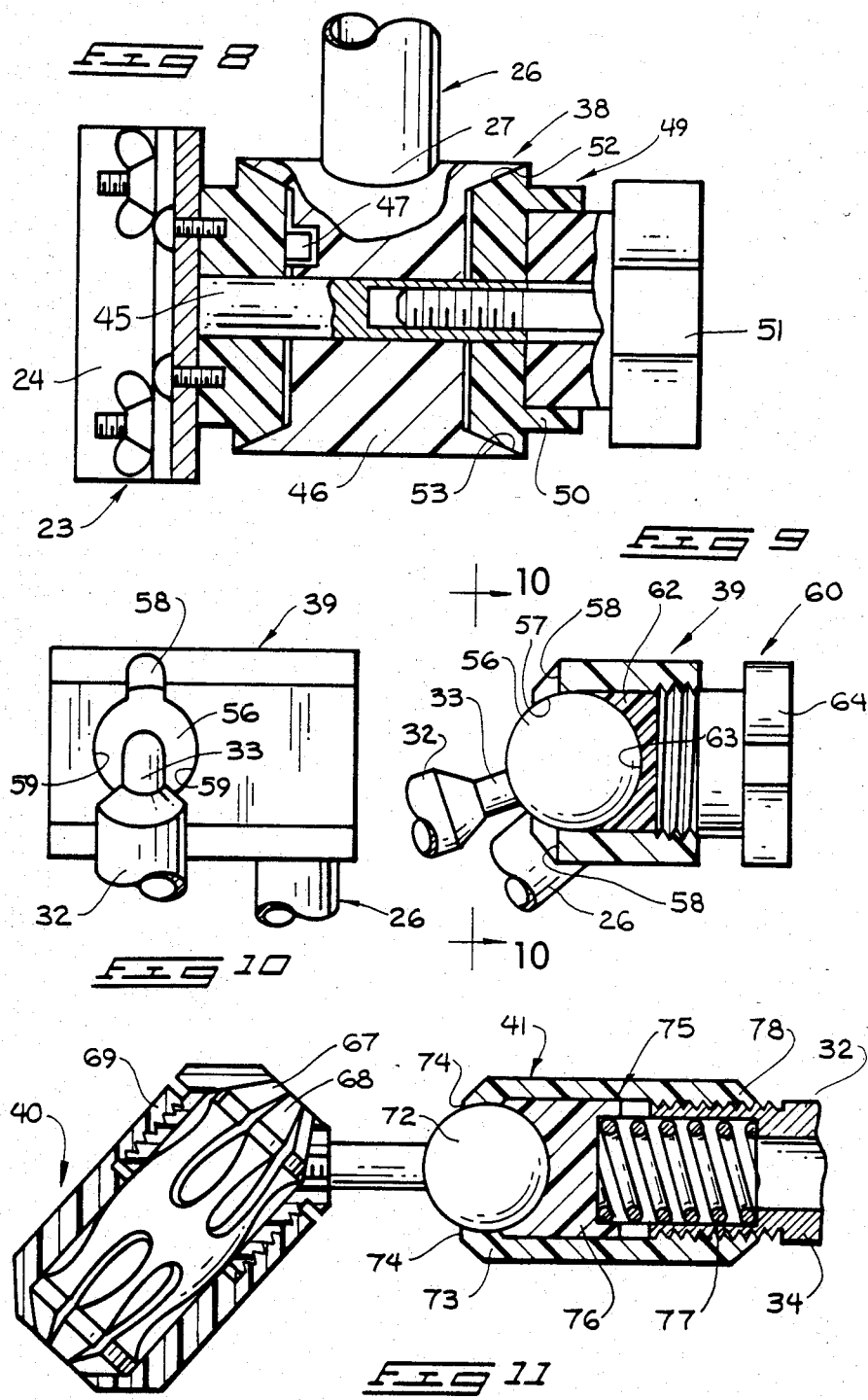

THERAPEUTIC AID

FIELD OF THE INVENTION

This invention relates to mechanical therapeutic development of fine, medium, and gross motor movements of a patient's arms.

BACKGROUND OF THE INVENTION

In physical rehabilitation, remediation of a motor movement impairment or a developmental disability is a slow, tedious, and expensive process. Therapists may achieve remediation through supervising repeated patient exercises, with "damping" (resistance to enhance muscle development) provided manually by the therapist. Such "damping" is sometimes aided by simple mechanical devices such as weights.

A critical aspect of this process is accuracy of the repeated movements. Inaccurate movements inhibit learning processes and prolong the rehabilitation period. This increases the stress level induced by boredom for the patient and increases demand for the therapist's direct attention. There is therefore a need for a device useful in assisting development of impaired or disabled muscles that will reduce the time for remediation by eliminating inaccurate movements, reduce or eliminate stress and boredom for the patient, and decrease the need for individual attention by the therapist.

Until advent of the present invention, there has been no single product which offers repetition, resistance, and accuracy required for fast and effective remediation without involving excessive individual attention by therapists. Solutions to the problem have only been partially provided by products which supply accuracy with repetition such as stencils and stencil-like products. However, they do not assist with selected reistance to movement. Devices or apparatus that do supply such resistance are typically weights which are attached to the wrist. The primary intent of the weights is to hold the wrist down. They make writing difficult and do nothing to dampen motion of the fingers and hands or to dampen lateral motions.

U.S. Pat. No. 46,827 to Squeir discloses a device for use in developing penmanship or fine scroll work. An apparatus is described for rotating or oscillating a drawing surface beneath an elbow arrangement for guiding the wrist and hand of the user. The arrangement appears to have adjustments to facilitate lateral movement of the elbow arrangement over the drawing surface.

U.S. Pat. No. 389,053 to Brown and U.S. Pat. Nos. 251,206 and 745,100 to Forbush also disclose mechanical apparatus for use in training individuals in penmanship and assist in training or conditioning finger and hand motions.

U.S. Pat. No. 3,929,462 to Karmin discloses a pantograph arrangement by which a teacher may grasp one stylus while a student grasps a remaining stylus mounted in the pantographic linkage. Movement of the teacher's hand is transmitted through the linkage to guide the student's hand. This device and disclosure recognize the problem and provides adequate solutions only where the teacher or therapist's time can be entirely devoted to the individual patient.

U.S. Pat. No. 3,425,140 to Dillon et al discloses a teaching machine utilizing servos mechanically attached to a stylus. The servos produce electronic signals that can be recorded and monitored for the purpose of giving audio, visual and kinesthetic feedback. Playback may be simultaneous or the recorded motions may be played back later. The Dillon patent recognizes the need for such a device but does not indicate provisions for offering a selected resistance to such motion for training and developing muscles and coordination of the user's arm, hand and fingers.

U.S. Pat. No. 3,690,020 to McBratnie discloses another electrical responsive instructional device for children with learning disabilities. This disclosure recognizes the need for a device that will provide for audio reinforcement for correctly following a stenciled pattern with a stylus sensor.

The above references independently recognize individual problems facing the therapist and patient needing training of specific muscle groups, especially in the area of the hand. The problem remains, however, of obtaining some specific apparatus by which fine, medium and gross motor movements of hand or the entire arm, including the hand, may be developed by specifically applied selected resistance to motion ("damping") without requiring other than minimal setup time by a therapist.

BRIEF DESCRIPTION OF THE DRAWINGS

A preferred form of the present invention is illustrated in the accompanying drawings in which:

FIG. 1 is a pictorial view illustrating the present invention in operation;

FIG. 2 is a fragmented and partially sectioned view showing an adjustment mechanism for the present invention and taken along a section indicated by the line 2—2 in FIG. 3;

FIG. 3 is a side elevation view of the present device;

FIG. 4 is a diagrammatic view illustrating angular motion capabilities for the two arm members of the present invention as seen from the side;

FIG. 5 is a view similar to FIG. 4 only as seen from above to indicate lateral motion capabilities;

FIG. 6 is an enlarged top plan view of a tool holder for the present invention;

FIG. 7 is a side elevation view of the tool holder shown in FIG. 6;

FIG. 8 is a fragmented sectional view taken through a shoulder joint and base member for the present invention;

FIG. 9 is a sectional view through an elbow joint of the present invention;

FIG. 10 is a view as seen from line 10—10 in FIG. 9; and

FIG. 11 is an enlarged sectional view of the tool holder taken along line 11—11 in FIG. 6.

DETAILED DESCRIPTION OF A PREFERRED EMBODIMENT

In compliance with the constitutional purpose of the Patent Laws "to promote the progress of science and useful arts" (Article 1, Section 8), applicant submits the following disclosure of the invention.

FIG. 1 indicates a basic form of the present device which is indicated therein by the reference numeral 10. The present device 10 is shown mounted to a stationary object such as a chair back 11. The unit extends forwardly from the chair back 11 toward a desk 12. It is to be operated by the user for the purpose of developing the engaged arm 13 including (but not restricted to) the shoulder 14, upper arm 15, elbow 16, forearm 17, wrist 18, and hand 19. The present device 10 can be so mounted to other stationary objects to offer a selected frictional resistance to motion of the arm, and thereby aid in developing fine, medium and gross motor movements.

It is pointed out that the arrangement illustrated in FIG. 1 is exemplary only. Other arrangements are also envisioned. For example, the device could as easily be mounted to the desk 12 and extend toward the user for grasping. The same or varied resistances could be applied for the same purposes. However, in a desk mounted orientation, the elements of the arm will be fully visible and thereby offer immediate kinesthetic feedback to the user as it moves directly in response to motion of the user's arm.

A base member 23 is generally illustrated in FIGS. 3 and 8 for the purpose of securing the device 10 to stationary objects. To this end, the base 23 includes a clamp structure 24. The configuration of the clamp structure 24 may vary with the object to which the device is to be mounted. The clamp can therefore vary in configuration to fit particular installation requirements. It is only necessary that the base be secured by the clamp in such a manner that it will remain stationary relative to the object 11.

An upper arm member 26 is pivotably mounted to the base. The upper arm member 26 is elongated, extending from a proximal or shoulder end 27 to a distal or elbow end 28. Member 26 is provided in two telescopic sections 29 selectively held together by a threaded clamp collar 30 (FIG. 2). The clamp collar can be loosened to release clamping forces between the telescopic sections and allow them to slide longitudinally relative to one another. This facilitates adjustment of the overall length for the upper arm member. It is preferred that the member length be adjustable between 19 and 23 inches.

A forearm member 32 is included with the device 10. The forearm member 32 is constructed somewhat similarly to the upper arm member 26. It is elongated, extending from a proximal or elbow end 33 to a distal or wrist end 34. Member 32 is also constructed of telescoping sections 36. These sections are selectively secured by a threaded clamp collar 36 to establish a prescribed length. The clamp collar and telescoping sections facilitate adjustment of the overall length of the forearm member between approximately 22 to 32 inches.

A shoulder joint means 38 pivotably connects the upper arm member 26 to the base 23 to permit pivotal motion of the upper arm member 26 about a fixed shoulder axis. An elbow joint means 39 articulates the forearm member 32 and upper arm 26. A grip means 40 may be provided at the wrist end 34 of the forearm member 32 to be grasped or otherwise attached to the head or arm of the user. Grip means 40 is mounted by a wrist joint means 41 to facilitate rotary motion of the wrist, hand or fingers connected with the grip means 40.

Details of the shoulder joint means 38 are illustrated in FIG. 8. Pivotal motion determined by the shoulder joint means is best illustrated in FIG. 4.

The shoulder joint means 38 includes an axle member 45 that extends rigidly outward from the base 23. The axle member 45 rotatably receives a hub 46. Hub 46 freely rotates on the axle 45 and securely mounts the shoulder end 27 of upper arm member 26. Means is provided such as a pin 47 formed in a slot and fixed relative to the base 23 for limiting relative angular motion of the hub 46 and attached upper arm member 26. The slot and pin arrangement as shown in FIG. 4 preferably limit angular motion of the upper arm member 15 within an arc of approximately 85° about the shoulder axis. This angular limit allows significant up and down motion (flexion and extension) of the upper arm 15 while the fixed axis prevents the entire structure from pivoting out of easy access by the user.

A first selective resistance means 49 is provided in the shoulder joint means 48 for adjustment to provide selective resistance to pivotal motion of the upper arm member about the shoulder pivot axis. The first selective resistance means includes a rotatively stationary shoulder brake member 50. Member 50 is secured against rotation about the axle member 45 by a keyway and key, or other attachment mechanisms by which relative rotary motion between the two is prevented.

Axial displacement of the brake member 50, is made possible by means such as a threaded knob 51 on the axle. The knob 51 can be turned to selectively move the brake member against or away from the hub 46. Both brake member 50 and hub 46 include inclined interfitting surfaces 52, 53, respectively. These surfaces act against one another when pressure is applied by the knob 51. The "wedging" action that increases kinetic friction between the rotatively stationary brake member and pivotable hub as the knob is tightened. The friction will decrease as the knob 51 is loosened.

The elbow joint means 39 is indicated in substantial detail by FIGS. 9 and 10. It includes a ball member 56 preferably secured to the elbow end 33 of forearm member 32. The ball member 56 is received within a complementary socket member 57 for relatively free rotary motion about the center point of the ball.

The socket member 57 includes abutment surfaces 58 and 59 (FIG. 8) for limiting angular motion of the attached forearm member 32 about the center point of the ball 56. Specifically, abutment surfaces 58 limit the angle through which the forearm member 32 will rotate toward and away from the base and shoulder joint members 38 (flexion and extension). This angle is preferably set to approximately 95°. This angle, coupled with the 85° pivot angle capability of the upper arm member, allows a considerable amount of forward, rearward, and up and down motion of the user's arm and hand.

Slightly less lateral motion is tolerated by abutment surfaces 59. These surfaces permit angular motion through an angle of approximately 80° for lateral movement of the forearm member 32, sufficient for abduction and adduction of the user's arm at the forearm. The angle will allow the patient's arm to cross the body center line yet is sufficiently restricted to prevent the forearm member from swinging laterally out of reach.

It is pointed out that the abduction and adduction (lateral) motions are accepted at the elbow joint means 39 rather than the shoulder joint means 38. It has been found that this is allowable and in fact desirable since facilitating such motion at the shoulder joint could result in the upper arm member striking the user's head, especially when used in the manner indicated in FIG. 1.

A second selective resistance means is provided at 60 for selection of rotational resistance of the forearm member 32 about the center point of the ball 56. The second selective resistance means 60 may include a friction brake member 62. It is slidably engageable along a concave surface 63 thereof with the similarly shaped spherical surface of ball 56.

The brake member is movably received within the socket and may be selectively urged against the ball 56 by means such as a threaded knob 64. The knob 64 can be turned to press or release axial pressure against the brake member to increase or decrease kinetic friction between the two members. This frictional resistance can be selectively varied from minimal, almost unnoticeable friction to a "locked up" situation where it becomes very difficult if not impossible for the user to pivot the two arm members 26, 32 relative to one another about the elbow joint.

A grip means 40 is illustrated in detail by FIG. 11. It should be understood, however, that the structure shown is merely exemplary and that other grips or like attachment devices can be mounted to the wrist end of the forearm member for a multitude of therapeutic purposes. Means 40 is exemplified in FIG. 11 as a tool holder 67. It has a multitude of uses for securing various devices to the unit in addition to providing a handy gripping surface for the user's hand. Hands not having gripping capability can be selectively attached by straps or other mechanisms to the tool holder 67 or whatever form of grip means 40 is selected for the wrist end 34.

The tool holder 67 shown includes a chuck 68 that is selectively opened and closed by a clamp member 69 to securely hold any of several common utensils used in remediation exercises for motor dysfunction. For example, a pencil could be secured within the chuck 68. Similarly, eating utensils such as spoons have also been secured in a similar chuck.

The wrist joint means 41 is provided to articulate the grip means 40 and forearm member 32. It includes a ball 72 on the tool holder 67 and a socket member 73 at the wrist end of forearm member 32. The ball is rotatably secured by the socket member for selected rotation about its center. Abutments 74 (FIGS. 6, 7, and 11) limit angular rotary motion of the tool holder with respect to the forearm member. The inclusive angle through which the tool holder may pivot is selected to be approximately 80°. This angle facilitates free motion of the fingers and hand and allows for pronation and supination of the forearm and upper arm.

A third selective resistance means 75 is provided at the wrist joint means 41 for selectively resisting rotary motion thereof in relation to the forearm member 32. The third selective resistance means 75 may consist of a friction brake member 76 that is somewhat similar to the brake member 62 described earlier. Member 62 is movably received within the socket member 73 and is selectively urged by means of a coil spring 77 against the ball 72. The compressive tension of the coil spring 77 is selectively varied by the axially positioning the socket 73 which is threadably engaged on the forearm member. The socket member can be turned to increase or decrease the axial forces applied against the brake member 76, correspondingly affecting the frictional resistance to motion between the two members.

It is preferred that the three selective resistance means described above be constructed of a fairly rigid yet low friction material. One such material that has functioned well in this regard is ultrahigh molecular weight polyethylene. The slidably engaged, independently moving members at each joint are preferably constructed of the same material, which is selected for its low friction coefficient and wear resistance. The low coefficient of friction allows for relatively free motion of the individual members when not resistance is desired. In addition, the low friction coefficient reduces the amount of force normally required to initially overcome resistance to motion. The result is a smooth, flowing motion that begins easily rather than abruptly as experienced where materials having high friction coefficient were used for the various members. The wrist and arm members will therefore begin movement once the selected resistance is overcome, without requiring an excessive force to overcome a "set" established when the respective members are at rest. This is especially important since one of the purposes of the device is to teach smooth, uniform movements. "Jerky" or abrupt motion would distract from this purpose.

The low friction material serves to "dampen" involuntary movements and offer even, steady resistance to other motions selected for purposes in developing or training specific muscle groups. For example, where only finger and wrist muscles are of concern, only the third selective resistance means 75 need be involved. The first and second can be released to the point where the arm members will pivot freely relative to one another and about the shoulder joint. Or they can be tightened to the point where only wrist and finger motion is allowed. Either situation can be adjusted by the therapist depending upon the particular needs of the individual patient. Further, as muscles continue to develop, increasing resistance can be applied to further develop and condition the muscles concerned.

The present device can be used in conjunction with other currently available therapeutic training apparatus such as stencils or electronic feedback mechanisms. But, whatever the use, the present device requires only minimal attention of the therapist and this only at the initial or "setup" phase where the various adjustments are made to suit the individual. The individual may then be left with minimal supervision to accomplish whatever tasks the therapist has set. The selected resistances will remain consistent and the gripping member will always remain fully within access to the patient.

As the patient works with the present device, an added benefit is gained. The patient is able to watch the responding motions of the arm members 26, 32 and gripping device. They provide kinesthetic feedback that is useful both in reducing boredom in the patient and as reinforcement by mimicking both desired and undesired motions. The damping effect through the joints, however, substantially minimizes undesired motion and so more positive than negative reinforcements are experienced by the patient.

In compliance with the statute, the invention has been described in language more or less specific as to structural features. It is to be understood, however, that the invention is not limited to the specific features shown. The means and construction disclosed herein merely exemplify a preferred form of putting the invention into effect. The invention is, therefore, claimed in any of its forms or modifications within the proper scope of the appended claims, appropriately interpreted in accordance with the doctrine of equivalents.

I claim:

1. A therapeutic device for use in developing fine, medium and gross motor movements of a patient's arm and hand, comprising:
   a base;
   means on the base for securing the base to a relatively stationary object such as a chair or desk;
   an elongated upper arm member having a shoulder end and a distal end;
   shoulder joint means on the base mounting the upper arm member at the shoulder end thereof for pivotal movement about a single shoulder pivot axis transverse to the upper arm member between prescribed angular limits;

first selective resistance means on the shoulder joint means, for affecting flexion and extension of the patient's arm by providing even continuous selective resistance to pivotal motion of the upper arm member about said shoulder pivot axis in relation to the base;

an elongated forearm member having a distal end and a proximal end;

elbow joint means articulating the forearm member and upper arm member at their respective proximal and distal ends for three dimensional rotary motion between prescribed angular limits about a center point;

second selective resistance means on the elbow joint means, for affecting adduction and abduction of the patient's arm by providing selective even continuous resistance to three dimensional pivotal motion of the forearm member about said center point; and grip means at the distal end of the forearm member for access by the patient's arm such that the patient's arm can be moved against selective resistance set by the first and second resistance means through an area defined by the shoulder and elbow joint means.

2. The therapeutic device as claimed by claim 1 wherein the first selective resistance means includes first stop means for limiting the upper arm member is to pivotable motion through an angle of approximately 85° about the shoulder pivot axis.

3. The therapeutic device as claimed by claim 1 wherein the second selective resistance means includes second stop means for limiting the forearm member to three dimensional rotational motion through an inclusive angle between approximately 80° to 95° about the center point of the elbow joint means.

4. The therapeutic device as claimed by claim 3 wherein the second stop means limits the forearm member to rotary motion toward and away from the shoulder joint means through an angle of approximately 95°, and lateral rotary motion about the center point of the elbow joint means in an arcuate path normal to the upper arm member through an angle of approximately 80°.

5. The therapeutic device as claimed by claim 1 further comprising means for selectively extending the upper arm member to selective lengths between 19 and 23 inches.

6. The therapeutic device as claimed by claim 5 further comprising means for selectively extending the forearm member to selective lengths between 22 and 32 inches.

7. The therapeutic device as claimed by claim 1 further comprising means for selectively extending the forearm member is extendable to selective lengths between 22 and 32 inches.

8. The therapeutic device as claimed by claim 1 wherein the grip means is comprised of a tool holder means at the distal forearm end for grasping by the patient's hand and for releasably holding a selected tool such as an eating utensil or writing instrument.

9. The therapeutic device as claimed by claim 1 further comprising wrist joint means mounting the grip means to the distal forearm end for limited three dimensional rotary motion about a wrist joint center; and third selective resistance means on the wrist joint means, for affecting rotation of the patient's wrist by providing selective resistance to rotary motion of the grip means about the wrist joint center.

10. The therapeutic device as claimed by claim 9 wherein the grip means includes stop means for limting rotary motion about the wrist joint center in three dimensions through an angle of approximately 80°.

11. The therapeutic device as claimed by claim 1 wherein the elbow joint means is formed of a ball member affixed to one of the arm members, and a socket member rotatably receiving the ball member and affixed to the remaining arm member; and wherein the socket member includes abutment surfaces thereon for limiting rotary motion of the ball member in relation thereto.

12. The therapeutic device as claimed by claim 11 wherein the second selective resistance means includes a friction brake member movably mounted to the socket member and engageable against the ball member; and means for selectively urging the friction brake member against the ball member.

13. The therapeutic device as claimed by claim 12 wherein the ball member and the brake member are formed of identical low friction material.

14. The therapeutic device as claimed by claim 13 wherein the low friction material is a low friction plastic such as ultrahigh molecular weight polyethylene.

15. The therapeutic device as claimed by claim 1 wherein the shoulder joint includes an axle member centered on the shoulder pivot axis and mounted to the base; a hub on the upper arm member pivotably mounted on the axle member, and means between the axle and hub for limiting motion of the hub and upper arm about the shoulder pivot axis.

16. The therapeutic device as claimed by claim 15 wherein the first selective resistance means is comprised of a rotatively stationary shoulder brake member mounted to the axle and movable against the hub member; and means on the axle operable to selectively urge the brake member against the hub member.

17. The therapeutic device as claimed by claim 16 wherein the hub member and shoulder brake member are formed of low friction material.

18. The therapeutic device as claimed by claim 17 wherein the low friction material is a low friction plastic such as ultrahigh molecular weight polyethylene.

19. A therapeutic exercise device for use in developing motor movements of the hand and arm of a patient, comprising:

handgrip member for contact with the patient's hand;

an elongated forearm member including a proximal elbow end and a distal wrist end;

wrist joint means mounting the handgrip member to the forearm member at the proximal wrist end for movement thereon corresponding directly to adduction, abduction, flexion, extension, pronation, and supinating motions of the patient's hand;

an elongated upper arm member including a proximal shoulder end and a distal elbow end;

elbow joint means mounting the upper arm member at the distal elbow end thereof to the forearm member at the proximal elbow end thereof, for relative motion corresponding directly to flexion, extension, abduction, adduction, pronation, and supination of the patient's arm at the elbow thereof;

a base member rigidly mountable to a stationary object such as a chair or desk; and shoulder joint means mounting the proximal shoulder end of the upper arm member to the base member for motion corresponding directly to flexion and extension of the patients arm at the shoulder thereof.

20. The therapeutic exercise device as claimed by claim 19 further comprising brake means at each of said joint means selectively and individually operable to evenly and continuously resist motion of adjacent members relative to one another.

21. The therapeutic device as claimed by claim 20 wherein the various joint means and brake means are formed of a low friction material.

22. The therapeutic exercise device as claimed by claim 19 further comprising angular motion limiting means at each joint means for confining motion of the various members mounted thereto within prescribed angular limits.

23. The therapeutic exercise device as claimed by claim 19 further comprising length adjustment means on the forearm and upper arm members selectively operable to increase or decrease their individual lengths.

24. A therapeutic exercise device for use in developing motor movements of the hand and arm of a patient, comprising:
handgrip member for contact with the patient's hand;
an elongated forearm member including a proximal elbow end and a distal wrist end;
wrist joint means mounting the handgrip member to the forearm member at the proximal wrist end for angular movement of the handgrip member to correspond directly to adduction, abduction, flexion, extension, pronation, and supinating motions of the patient's hand;
an elongated upper arm member including a proximal shoulder end and a distal elbow end;
elbow joint means mounting the upper arm member at the distal elbow end thereof to the forearm member at the proximal elbow end thereof, for limiting angular motion of the forearm member relative to the upper arm member to correspond directly to flexion, extension, abduction, adduction, pronation and supination of the patient's arm at the elbow thereof;
a base member rigidly mountable to a stationary object such as a chair or desk;
shoulder joint means mounting the proximal shoulder end of the upper arm member to the base member for angular motion of the upper arm member about a shoulder pivot axis to correspond directly to flexion and extension of the patient's arm at the shoulder thereof; and
brake means at each of said joint means selectively and individually operable to evenly and continuously resist motion of adjacent members relative to one another.

* * * * *